United States Patent [19]

Mihm et al.

[11] Patent Number: 5,378,413
[45] Date of Patent: Jan. 3, 1995

[54] PROCESS FOR PREPARING MICROCAPSULES HAVING GELATIN WALLS CROSSLINKED WITH QUINONE

[75] Inventors: James W. Mihm, Annapolis; George I. Loeb, Bethesda; Elizabeth G. Haslbeck, Annapolis, all of Md.

[73] Assignee: The United States of America as represented by the Secretary of the Navy, Washington, D.C.

[21] Appl. No.: 6,595

[22] Filed: Jan. 21, 1993

[51] Int. Cl.⁶ ............... A01N 25/28; B01J 13/10; B01J 13/20
[52] U.S. Cl. .................. 264/4.3; 264/4.33; 424/406; 424/408; 428/402.2; 428/402.22; 514/963; 524/178
[58] Field of Search ............. 264/4.3, 4.33; 428/402.2, 402.22; 514/963; 424/406, 408

[56] References Cited

U.S. PATENT DOCUMENTS

| | | | |
|---|---|---|---|
| 2,800,457 | 7/1957 | Green et al. | 428/402.2 |
| 2,800,458 | 7/1957 | Green | 264/4.3 |
| 3,265,629 | 8/1966 | Jensen | 264/4.3 |
| 3,697,437 | 10/1972 | Fogle et al. | 264/4.3 X |
| 4,082,688 | 4/1978 | Egawa et al. | 264/4.3 |
| 4,253,877 | 3/1981 | Miale et al. | 264/4.3 X |

OTHER PUBLICATIONS

E. G. Haslbeck et al., "Microencapsulation of Biocides For Use in Antifouling Coatings," Proceedings of the 16th International Symposium on Controlled Release of Bioactive Materials, pp. 273–274 Aug. 1989.

Rose et al.: *The Condensed Chemcial Dictionary*, Sixth Edition, Reinhold Publ. Corp., New York (1961), p. 1160.

*Primary Examiner*—Richard D. Lovering
*Attorney, Agent, or Firm*—Gary G. Borda

[57] ABSTRACT

A process for conveniently producing microcapsules containing a gelatin wall crosslinked with quinone and a core of an active compound such as a fouling reducing agent, particularly a tributyl tin chloride, involves use of a simple or complex coacervation technique. The quinone crosslinking provides microcapsules of excellent strength, storage stability, and resistance to aqueous exposure, such that the rate of release of the fouling reducing agent can be controlled with precision.

10 Claims, No Drawings

PROCESS FOR PREPARING MICROCAPSULES HAVING GELATIN WALLS CROSSLINKED WITH QUINONE

BACKGROUND OF THE INVENTION

Field of the Invention

The present invention relates to a process for forming microcapsules and to the microcapsules so produced and to the use of such microcapsules in paint compositions. More particularly, the present invention relates to microcapsules having a wall containing gelatin crosslinked with quinone, wherein the core contains a fouling reducing agent such as a tributyl tin compound.

Description of Related Art

Microencapsulation involves the application of a coating around a microscopic phase of a liquid or solid core material. The first applications of microencapsulation were in carbonless copying papers and in the controlled release of drugs. Many other applications have since been explored such as described by Bayless, R., "Microencapsulation in New Areas," Chemical Engineering News, Vol. 52, p.16, August 1974.

The use of microencapsulated compounds has many advantages over the use of unencapsulated compounds. In particular, the microencapsulation separates the core material from its environment and provides a controlled release rate. The release rate of the core material and the diffusion of the core material through the capsule wall can be controlled by varying the wall composition and/or the degree of crosslinking of the walls. Furthermore, if a material is encapsulated, its useful life may be significantly extended. Also, if a material is toxic and hence difficult to handle, encapsulation of the material may reduce the threat of acute exposure and allow for easier handling.

Since many fouling reducing agents are extremely toxic and there is a desire to have these compounds act over extended periods of time, encapsulation of such compounds is desirable. Such encapsulation should serve to control the release rate of the agent and to avoid an initial high release of agent which could be environmentally unacceptable. In particular, tributyl tin compounds, such as tributyl tin chloride (TBTCl), are extremely toxic and thus excellent candidates for encapsulation.

Work by Noren et al. ("Investigation of Microencapsulated Fungicides for Use in Exterior Trade Sales Paints," *Journal of Coatings Technology*, 58:724 (1986)) and Porter et al. ("Extended Control of Marine Fouling," Applied Biochemistry and Biotechnology, 9:439-445, (1984)) indicate that two different coating formulations have been tested which contain bioactive microcapsules. Noren et al. have formulated an exterior paint containing microcapsules with urea-formaldehyde treated gelatin walls surrounding fungicidal compounds. The encapsulation of the fungicides allows for control of both the release and volatility of the active ingredient.

Porter et al. describe formulations of a vinyl antifouling coating containing microcapsules having gelatin and gum arabic walls crosslinked with glutaraldehyde, wherein the core is a tributyl tin chloride antifoulant. These microcapsules degrade in an aqueous environment and hence are not very useful in aqueous environments.

Haslbeck et al. in: Proceeding of the 16th International Symposium on controlled Release of Bioactive Materials, pages 273-274 (1989), describe crosslinking a gelatin/polyphosphate or gelatin/gum arabic microcapsule with glutaraldehyde and quinone. That document does not describe a method of conveniently producing such microcapsule.

Accordingly, there has been a need to find an improved microcapsule which can be conveniently manufactured and is useful for encapsulating active compounds, such as fouling reducing agents, in particular tributyl tin compounds, wherein the microcapsules allow for excellent control of the release rate of the active core material. Furthermore, there is a need to provide an improved method of encapsulating TBTCl which, though being highly toxic, is one of the most effective fouling reducing agents known. There is a need to provide a method of producing microcapsules which results in a microcapsule exhibiting a controllable release rate and allowing for a reduced initial TBTCl release rate so as to continue its safe use in, for example, antifoulant coating compositions.

SUMMARY OF THE INVENTION

It is an object of the present invention to provide an improved microencapsulating process for encapsulating compounds, such as fouling reducing agents, with a capsule wall comprising gelatin, wherein the microcapsules are capable of being reduced to a powder and dispersed into a coating.

It is a further object of the present invention to develop a microcapsule particularly useful in antifouling paints which offers excellent control of the release of the core material from the capsule.

It is also an object of the present invention to provide an antifouling coating composition which contains a fouling reducing agent encapsulated in a shell, wherein the fouling reducing agent is released over time so as to impart excellent antifoulant characteristics to the coating over time.

In accomplishing the foregoing objectives, there has been provided, in accordance with one aspect of the present invention, a process of forming a microcapsule comprising the steps of:

a) emulsifying a core material in a solution of gelatin at about 50° C. so as to produce particles having a diameter of about 30 to about 100 microns, b) adding a polyanion to the emulsion, c) adjusting the pH of the emulsion to between about 4 and about 5 so as to allow coacervation, d) cooling the coacervate to room temperature so as to allow the coacervate to gel around the core material thus forming microcapsules with a wall comprising gelatin, and e) crosslinking said wall with a quinone.

In accordance with another aspect of the present invention, there is provided a method of producing microcapsules comprising the steps of:

a) emulsifying a core material with a solution of gelatin, b) adding a water-miscible alcohol or a salt to the gelatin solution to induce phase separation and coacervation, c) cooling the solution to gel a wall of gelatin around the core forming a microcapsule, and d) crosslinking the wall with a quinone.

In accordance with a further object of the present invention, there has been provided a microcapsule produced by each of these processes.

In accordance with another object of the present invention there has been provided a coating composition comprising a binder and a microcapsule which has a wall comprising gelatin which has been crosslinked with quinone, wherein said wall encapsulates an active material, preferably a fouling reducing agent, wherein the microcapsule has been produced by one of the above methods.

Further objects, features, and advantages of the present invention will become apparent from the detailed description of preferred embodiments which follows.

DETAILED DESCRIPTION OF THE PREFERRED EMBODIMENTS

The microcapsules of the present invention contain a core of an active material. The active material may be any material which has utility in an encapsulated form due to the desire to control the release of the compound and extend the useful life of the compound and/or due to the desire to avoid direct handling of the compound.

The active compound is preferably a fouling reducing agent. Any fouling reducing agent may be encapsulated, with particular preference being given to tributyl tin compounds, most particularly to tributyl tin chlorides. Mixtures of fouling reducing agents may also be encapsulated and mixtures of fouling reducing agents with other components, such as herbicides, can be encapsulated according to the invention. The microcapsules generally contain about 10 to about 20% by weight of wall material and about 80 to about 90% by weight of core material.

The walls of the capsule are formed from a polymeric material containing an amino group, preferably the polymeric material comprises gelatin. Any type of gelatin can be used. The gelatin is optionally associated with a polyanion, such as gum arabic or polyphosphate. As discussed below, the polyanion is present if a complex coacervation process is used to form the shell.

An important part of the present invention is that the polymeric walls be crosslinked with a quinone. Quinone itself and/or compounds containing a quinone moiety can be used to crosslink the gelatin. The quinone may be the sole crosslinker, that is quinone can be used alone without other crosslinkers such as aldehydes. Alternatively, the quinone crosslinking can be used in combination with other crosslinkers. In particular, use of quinone crosslinking following crosslinking with an aldehyde such as glutaraldehyde or formaldehyde has been found to be particularly useful. Other aldehydes can also be used which will crosslink the gelatin. The use of quinone as a crosslinker results in a microcapsule which is more stable in an aqueous environment than when an aldehyde crosslinker is used alone, and provides capsules walls with greater strength, allowing for excellent storage stability.

Quinone crosslinking of proteins has been used in the leather tanning industry as described in Spurr, K., Thesis, Cornell University, Ithaca, N.Y. (1958); Gustavon K. H., *The Chemistry of the Tanning Process.* Academic Press, N.Y. (1965); and Green R. W. JACS 75: 2729, (1953) as cited by G. Loeb, Ph.D Thesis, Cornell University, June 1960.

An important part of the present invention is the production of the microcapsules. It is preferred to use simple or complex coacervation microencapsulation techniques. Although these techniques are known per se, they are not known to form microcapsules as described herein. In particular, the ability to use coacervation processes depends upon numerous parameters including the properties of the core and how the wall material interacts with the core. Hence, much experimentation is needed to determine the processing parameters necessary for the coacervation.

Simple coacervation is a phase separation phenomena caused by decreasing the solubility of a hydrocolloid in a solvent. According to the present invention, the following process has been found useful. A gelatin solution, preferably.an aqueous solution, at about 40° to about 60° C. is emulsified with the core material. To the emulsion is added a water-miscible alcohol, such as ethanol or isopropanol, and/or a salt, such as sodium sulfate or ammonium sulfate, to induce phase separation. The emulsion is cooled to gel the wall around the core and then the wall is crosslinked as described above. If too much alcohol or salt is used, the gelatin will precipitate. However, if the amount of a coacervating agent is carefully controlled, a liquid polymer-rich phase can be produced which forms microcapsules.

Complex coacervation is a spontaneous liquid/liquid phase separation that can occur when oppositely charged polyelectrolytes are mixed in aqueous media. This phenomenon is limited to mixtures of polyelectrolytes that have a suitable ionic charge density and chain length. Accordingly, not all mixtures will form complex coacervates.

Coacervation processes are described by H. G. Bungenberg de Jong, Colloid Science II, H. R. Kruyt, ed., Elsevier Publishing Co., New York, N.Y., 1949, pp 232–480 and in U.S. Pat. Nos. 3,697,437 and 2,800,457.

Both simple and complex coacervation process can be used, however complex coacervation is the preferred method. In particular, after much experimentation with both simple and complex coacervation, the following complex coacervation process was found to give excellent results, with regards to the formed microcapsule. Complex coacervation as used in the present invention comprises emulsifying a gelatin, preferably an aqueous gelatin solution at a temperature of about 40° to about 50° C. with the core material, and then mixing the appropriate combinations of oppositely charged polyelectrolytes into the emulsion. Useful electrolytes include gum arabic, polyphosphates, alginate, carboxymethylcellulose, carrageenan, and/or ethylene/maleic anhydride copolymers. Coacervation and deposition of the wall around the core occurs upon proper adjustment of the pH and cooling. The resulting coacervate solution is characterized by a polymer rich coacervate phase and a polymer-poor phase. The coacervate is adsorbed by the core material and, on cooling, forms the gelled capsule wall. This process is described in more detail in the examples which follow.

The microcapsules of the present invention can be used in any desirable manner, and are particularly useful as an additive to an antifouling paint or coating system. The microcapsules are generally used in amounts which will impart the desired fouling reducing affect to the coating. Such amount is generally in the range of about 1 to 10% by weight of microcapsules based on the total weight of the coating composition. Paints based on organic films are particularly useful. Such paints include those containing a rosin and vinyl chloride/vinyl acetate copolymer binder. Coatings and paints containing the inventive microcapSule additionally may contain further ingredients conventionally used in antifouling coating systems.

In addition to the microcapsules described above, other types of microcapsules, such as those having a core of other fouling reducing agents or herbicides, can be added to the coating material. For instance, encapsulated herbicides, such as simazine, can be added to the coating so as to further control algal microfouling.

The invention will now be illustrated with reference to the following examples without being limited thereby.

EXAMPLE 1

This example illustrates the use of simple coacervation to form microcapsules. The core material used was a mineral oil, which was used to simulate the encapsulation of TBTCl oil. The procedure used was as follows:

1. 25 grams of gelatin were completely dissolved in 200 ml distilled water while placed in a water bath maintained at 55° C.

2. To the dissolved gelatin, 50 ml of heavymineral oil was added and allowed to equilibrate at 55° C.

3. Concurrently, a solution of 7% isopropyl alcohol was also heated in the water bath to 55° C.

4. The gelatin-oil mixture was then placed in a blender and mixed at the highest speed for 1 min. This step emulsified the oil in the gelatin mixture, resulting in oil spheres of approximately 50 to 100 μ diameter dispersed throughout the gelatin solution.

5. The blender speed was then reduced and the heated 7% alcohol solution added slowly to facilitate the phase separation. Discrete microcapsules form with the oil as the core material and the gelatin as the wall material.

6. The solution containing the gelatin-oil coacervate was then slowly poured into 2 liters of 7% isopropyl alcohol solution at about 10° C., with constant stirring, and maintained at 10° C. for 2 hours. The rapid cooling of the microcapsules serves to gel the gelatin coacervate around the oil drops. The mixture is allowed to stand for several hours whereupon the formed microcapsules float to the top with free coacervate/unreacted gelatin sinking to the bottom. The formed microcapsules are then rinsed to remove any unused gelatin.

7. Although at this point the gelatin capsules have gelled and remain discrete, they are not thermostable, and the capsules will not maintain their integrity when separated and dried. For this reason the gelatin capsules, while maintained at 10° C., were crosslinked with formaldehyde for 4 hours. The formaldehyde crosslinking serves to render the capsules heat stable by binding the amino sites of neighboring gelatin molecules.

8. The microcapsules may be further hardened by following the aldehyde step with an additional 4 hours of quinone treatment.

The first dried microcapsules using the formaldehyde crosslinking agent alone resulted in the capsules sticking together and being soft. These are not suitable for dispersion into an antifouling coating system. Increasing the amount of formaldehyde crosslink and the crosslinking time did not improve capsule integrity. It was also observed that the capsules could be easily broken, causing the oil to be released. To provide greater capsule wall integrity, the formaldehyde crosslinking step may be followed by additional crosslinking with quinone. It is believed that the addition of the quinone will greatly improve the integrity of the capsule wall.

EXAMPLE 2

This example illustrates the use of complex coacervation to form microcapsules. Initial experimentation involved encapsulating model oils (mineral oil or extra virgin olive oil) with gelatin/polyphosphate and gelatin/gum arabic to simulate the encapsulation of tributyltin chloride oil. Acid precursor gelatins were used with bloom strengths of either 160 or 280. The polyanions used were gum arabic or polyphosphate. A lipophilic blue dye (Oil blue-N) was dissolved in the oil to aid in monitoring microcapsule formation.

The procedures used were as follows:

1. A water bath was used to heat the following solutions and material to 50° C.:

| Gelatin/Polyphosphate (G/P) | Gelatin/Gum Arabic (G/GA) |
|---|---|
| 11% gelatin solution | 11% gelatin solution |
| 5% polyphosphate solution | 11% gum arabic solution |
| distilled water | distilled water |
| oil | oil |

2. To 800 milliliter (ml) beakers were added:

| | |
|---|---|
| 90.9 ml gelatin solution, 29.1 ml distilled H$_2$O, and 5–10 drops n-octanol (defoaming agent) | 60 ml gelatin solution 67 ml distilled H$_2$O, and 5–10 drops n-octanol (defoaming agent) |
| 3. A solution of 90 ml oil with <1 g Oil blue-N dye was added slowly to the gelatin solution and emulsified by rapid impeller stirring to desired droplet size of 30–100 microns. | A solution of 60 ml oil with <1 g Oil blue-N dye was added slowly to the gelatin solution and emulsified by rapid impeller stirring to the desired droplet size of 30 to 100 microns. |

An even distribution of droplets was achieved by stirring the above solution at high speeds for from 5–10 minutes.

| | |
|---|---|
| 4. 120 ml distilled H$_2$O and 20 ml polyphosphate solution were added. | 200 ml distilled H$_2$O and 67 ml gum arabic solution were added. |

5. Adjustment to a pH of about 4.0 to about 5.0, preferably 4.1 to 4.6, with acetic acid and/or sodium hydroxide, caused coacervate to form.

6. The mixture was cooled slowly at about 1° C. every ten minutes, to room temperature (about 23° C.) with minimal stirring. This allowed the coacervate phase to gel around oil droplets and form the walls. At this point these were embryo microcapsules which were not thermostable.

7. The microcapsules were rinsed with distilled water to remove excess coacervate which would cause agglomeration if allowed to remain.

8. The mixture was cooled to 5°–10° C. for 30 minutes in an ice bath; 5 ml 25% glutaraldehyde solution was added. This was allowed to come to room temperature,(about 23° C.) and the desired length of time to harden the microcapsule walls, making the microcapsules durable and less water-sensitive, and rendering them thermostable.

9. After about thirty to sixty minutes of crosslinking with the aldehyde, the microcapsules were crosslinked further with a saturated quinone solution for the desired length of time to produce microcapsules of excellent strength and minimal water-sensitivity, generally for 18 to 36 hours at room temperature. The quinone gives microcapsules of added strength and even less water-sensitivity than achieved with aldehyde crosslinking alone.

10. The microcapsules were rinsed and filtered.
11. Silica drying agent was used to aid in drying microcapsules to a free-flowing powder.

This procedure was used to encapsulate both mineral oil alone and combinations of TBTCl oil (94% pure as in Example 2) and mineral oil. Microcapsules with 16% and 0.27% TBTCl in mineral oil were successfully produced. These microcapsules were then tested for compatibility with paint systems.

Both types of TBTCl microcapsules, 16% TBTCl and 0.27% TBTCl, and mineral oil microcapsules for controls, were formulated into a coating system having the following composition:

Formula for approximately 1½ gallon:

| Rosin (grade WW) | 1600 g |
|---|---|
| Vinyl chloride/vinyl acetate copolymer | 460 g |
| TCP (Tri-cresyl phosphate) | 420 g |
| MIBK (Methyl iso-butyl Ketone) | 1380 g |
| Xylene | 960 g |
| Bentone 38 | 70 g |
| Propylene Carbonate | 22 g |

The experimental paints contained concentrations by weight of ten, six, and two percent of each type of microcapsules. These coatings were then applied to 3"×5" sand blasted G-10 epoxy fiberglass panels. The compatibility of the microcapsules with the paint system was evaluated by observing capsule integrity and clumping after mixing. Observations were made using a microscope at 15X total magnification.

The quinone crosslinking greatly increases the capsule wall strength as compared to aldehyde crosslinking and results in a capsule having greater resistance to aqueous environments, that is, there is not a premature breakdown in aqueous environments.

The TBT-containing capsules dispersed very well in the clear resin. The lack of pigment allowed observation of the capsules throughout the film thickness. Visual inspection verified that the capsules were compatible with the coating system since they did not rupture, even when the coating dried.

Results and Discussion

Using the complex coacervation techniques, a dry, free-flowing powder of microcapsules was obtained in each case which could readily be dispersed in the coating system. The size range of capsules in the slurry before drying was about 50–125 μm. The dried capsules tended to clump, and ranged in size from 65–300 μm. Small microcapsules (20–30 μm) of a more uniform size distribution can also be prepared.

The TBTCl microcapsules were of the same quality as the pure mineral oil capsules. That is, they appeared similar under 10X magnification, having the same relative shape and wall thickness. They also formed a comparable final dried powder.

Aldehyde cross-linking alone generally did not provide sufficient wall integrity and has inadequate stability in aqueous environments. Therefore, to provide greater strength and stability in aqueous environments, the aldehyde cross-linking step was followed by additional cross-linking with quinone. The quinone bonds are more stable in an aqueous environment. Dried capsules were left in jars at room temperature for several months and retained wall integrity. The dried capsules are characterized by non-leaky uniform walls.

Testing was conducted on the compatibility of the microcapsules with the pigment-free coating system described above. Both mineral oil and TBT capsules dispersed very well in the coating system. Visual inspection verified that the capsules were compatible with the coating system since they did not rupture or deform, even when the coating dried.

The invention has been described in detail with particular reference to preferred embodiments thereof but it will be understood that variations and modifications can be effected within the spirit and scope of the invention.

What is claimed is:

1. A process for preparing a microcapsule comprising the steps of:
    a) emulsifying a core material in an aqueous solution of gelatin at a temperature of about 40° C. to about 50° C. so as to produce particles having a diameter of about 30 to about 100 microns, said aqueous solution of gelatin comprising an acid precursor gelatin having a bloom strength between about 160 and about 280 and distilled water,
    b) adding an aqueous polyanion solution comprising distilled water and a polyanion to the emulsion,
    c) adding a pH adjusting agent selected from the group consisting of acetic acid, sodium hydroxide and a mixture of the two so as to adjust the pH of the emulsion to between about 4 and about 5 so as to allow coacervation,
    d) cooling the coacervate to room temperature at a rate of about 1° C. every 10 minutes so as to allow the coacervate to gel around the core material forming microcapsules with a wall comprising gelatin,
    e) rinsing said microcapsules with distilled water to remove excess coacervate,
    f) cooling said microcapsules for at least about 30 minutes at about 5° C. to about 10° C.,
    g) allowing said microcapsules to come to room temperature, and
    h) crosslinking said wall with a saturated quinone solution for about 18 to about 36 hours at room temperature.

2. A process as claimed in claim 1 wherein said core material comprises a fouling reducing agent.

3. A process as claimed in claim 2 wherein said fouling reducing agent is a solution of a tributyl tin compound in a mineral oil.

4. A process as claimed in claim 3, wherein said tributyl tin compound comprises tributyl tin chloride.

5. A process as in claim 1, wherein said aqueous solution of gelatin comprises about 9.1 parts by volume of said acid precursor gelatin and about 2.9 parts by volume of said distilled water, and said aqueous polyanion solution comprises about 12 parts by volume of said distilled water and about 2 parts by volume of polyphosphate.

6. (Amended) A process as in claim 1, wherein said aqueous solution of gelatin comprises about 6 parts by volume of said acid precursor gelatin and about 6.7 parts by volume of said distilled water, said aqueous polyanion solution comprises about 20 parts by volume of said distilled water and about 6.7 parts by volume of gum arabic.

7. A process as in claim 1, wherein said wall is additionally crosslinked with an aldehye for about 30 to about 60 minutes between stepd f) and g).

8. A process as in claim 7, wherein said aldehyde is selected from the group consisting of formaldehyde and glutaraldehyde.

9. A process as claimed in claim 1, wherein said pH is adjusted to between 4.1 and 4.6 during step c).

10. A process as in claim 1, further comprising after step h) the steps of rinsing and filtering the microcapsules and drying the microcapsules to produce a free-flowing powder.

* * * * *